US008292623B2

(12) United States Patent
Vandor et al.

(10) Patent No.: US 8,292,623 B2
(45) Date of Patent: Oct. 23, 2012

(54) SYSTEMS AND METHODS FOR SETTING PROSTHETIC POSTERIOR TEETH IN DENTURE PRODUCTION

(76) Inventors: Jory Brock Vandor, Winnipeg (CA); Gyula Victor Vandor, Medicine Hat (CA)

(*) Notice: Subject to any disclaimer, the term of this patent is extended or adjusted under 35 U.S.C. 154(b) by 0 days.

(21) Appl. No.: 12/777,854

(22) Filed: May 11, 2010

(65) Prior Publication Data

US 2010/0283168 A1  Nov. 11, 2010

Related U.S. Application Data

(60) Provisional application No. 61/176,966, filed on May 11, 2009.

(51) Int. Cl.
*A61C 13/10* (2006.01)
(52) U.S. Cl. ......................................................... 433/196
(58) Field of Classification Search .................... 433/34, 433/54–67, 190–196, 199.1, 201.1, 213; 264/16–19
See application file for complete search history.

(56) References Cited

U.S. PATENT DOCUMENTS

| | | | | |
|---|---|---|---|---|
| 4,337,039 A * | 6/1982 | Martin et al. | ................... | 433/60 |
| 4,413,978 A * | 11/1983 | Kurz | ................. | 433/6 |
| 4,725,233 A * | 2/1988 | Planert | ............................ | 433/15 |
| 6,139,321 A * | 10/2000 | MacCulloch | ................. | 433/196 |
| 2004/0131990 A1 * | 7/2004 | Doviack | ........................... | 433/60 |
| 2004/0191728 A1 * | 9/2004 | Miller | ........................... | 433/213 |
| 2006/0040232 A1 * | 2/2006 | Shoup | ............................ | 433/72 |
| 2006/0210945 A1 * | 9/2006 | Savic et al. | ..................... | 433/68 |

* cited by examiner

*Primary Examiner* — Cris L Rodriguez
*Assistant Examiner* — Matthew Seward
(74) *Attorney, Agent, or Firm* — Kyle R. Satterthwaite; Ryan Dupuis; Ade & Company Inc.

(57) ABSTRACT

Systems and methods for setting posterior prosthetic teeth in production of upper and lower dentures feature tooth blocks each having inner and outer bodies having upper and lower rows of recesses therein corresponding maxillary and mandibular prosthetic teeth. The recesses of the inner and outer bodies conform to lingual and buccul surfaces of the prosthetic teeth respectively and are shaped and positioned to establish proper positioning of the prosthetic teeth relative to one another when clamped between the bodies. The two tooth blocks accommodate respective ones of left and right prosthetic poster teeth sets. Connection elements between the tooth blocks allow adjustment and subsequent locking of the relative positioning between the left and right teeth sets before setting on mandibular and maxillary casts in an articulator. The two tooth blocks eliminate the need to individually position posterior teeth on each side of the jaw.

15 Claims, 8 Drawing Sheets

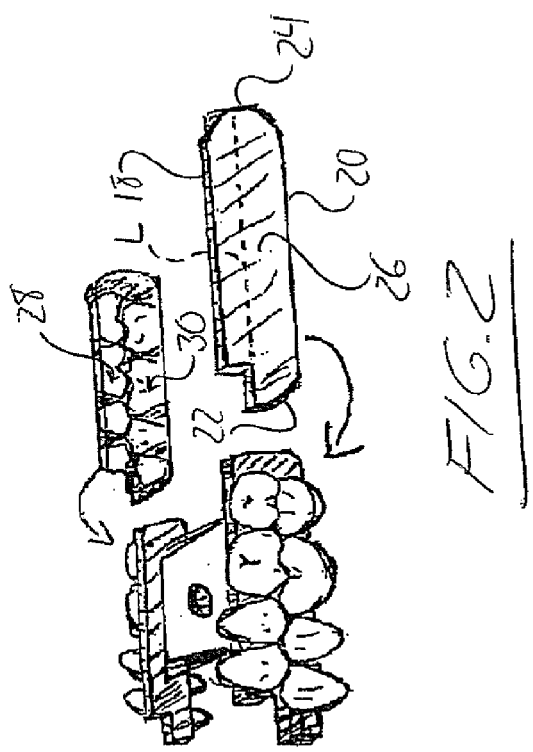
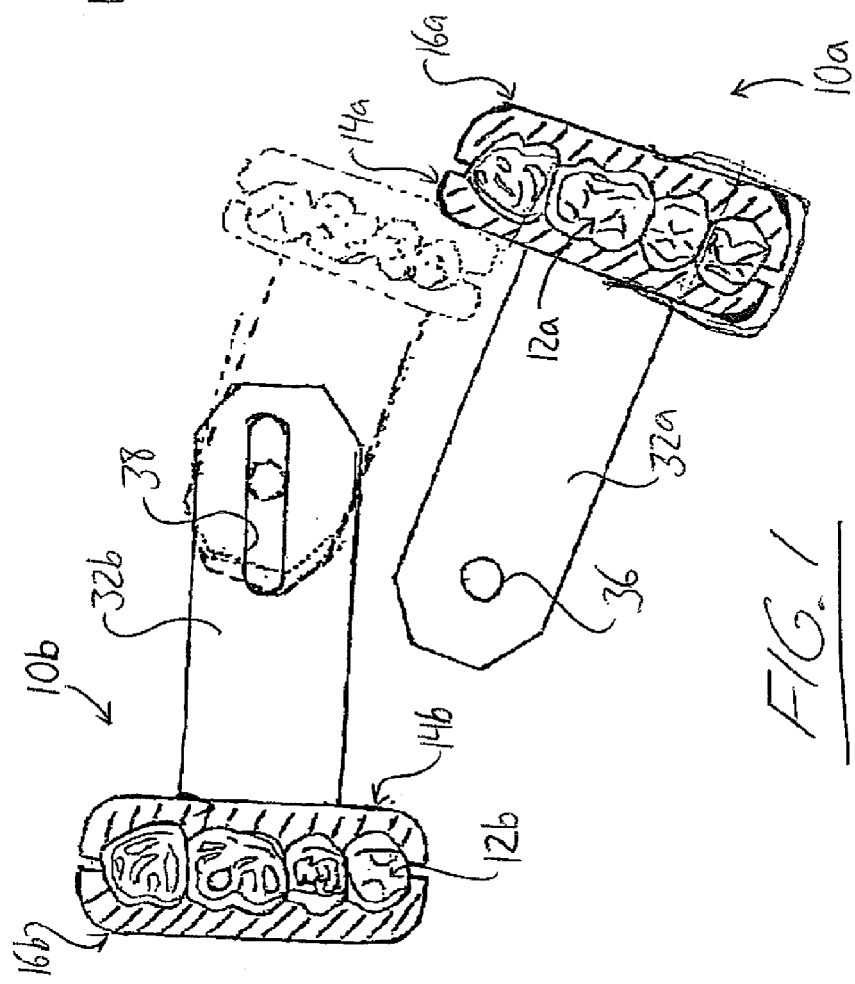

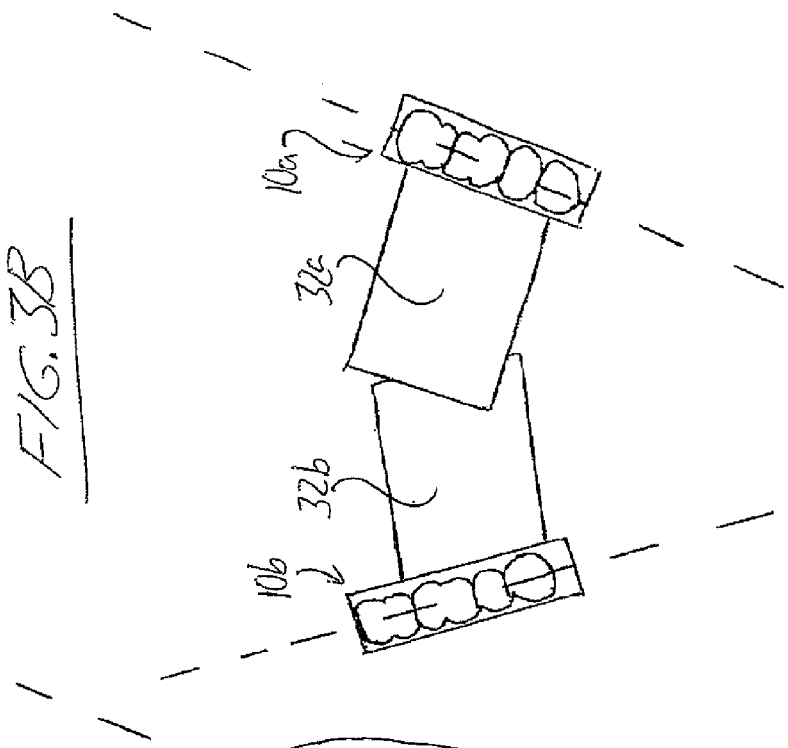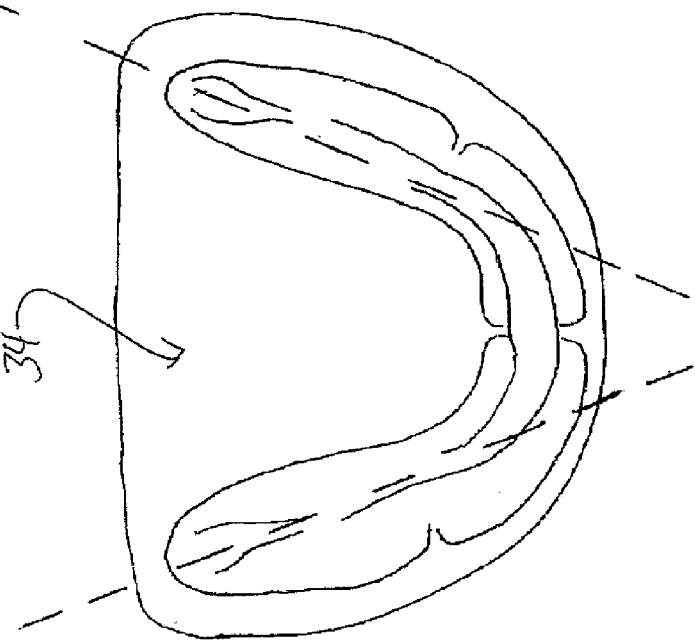

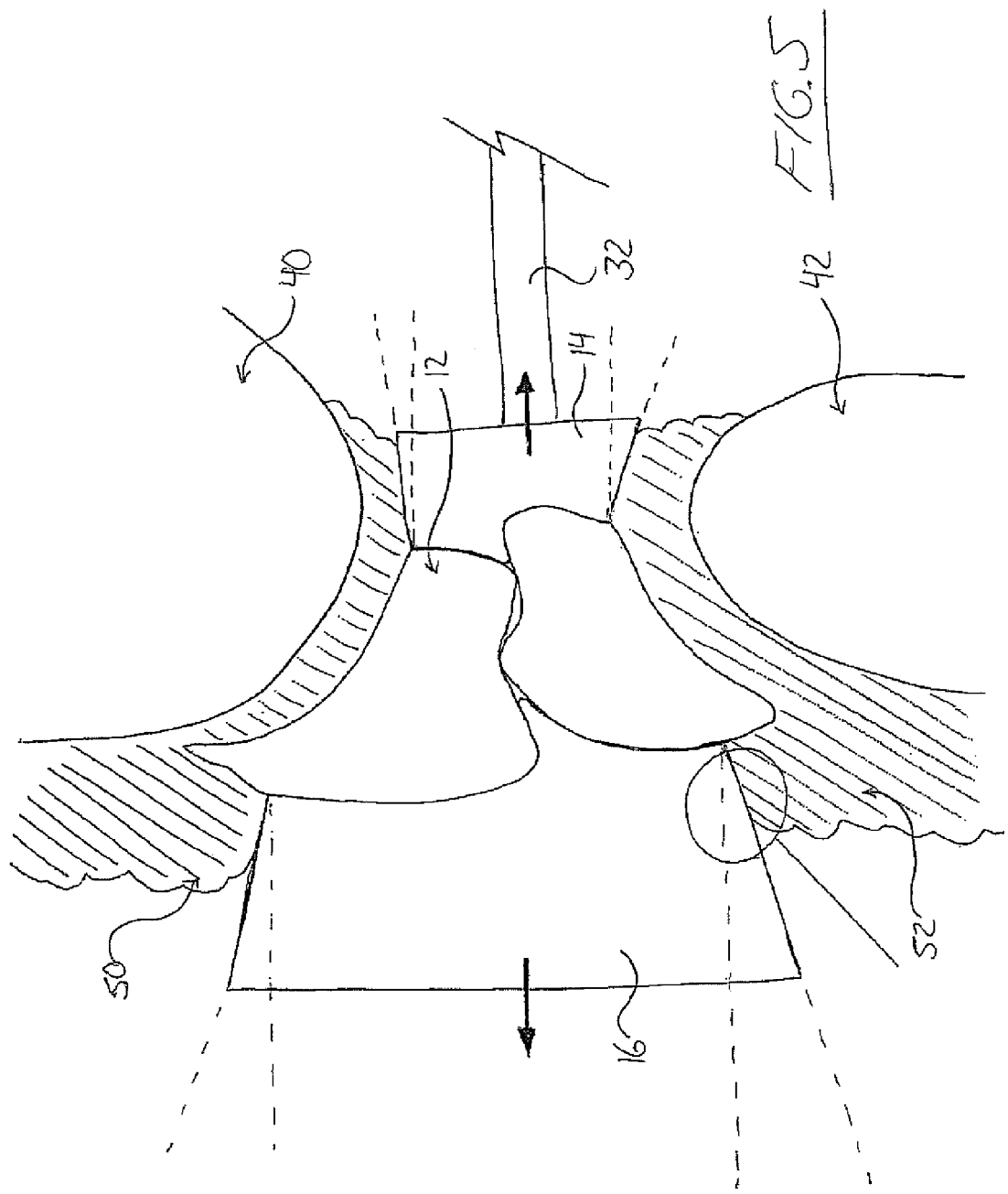

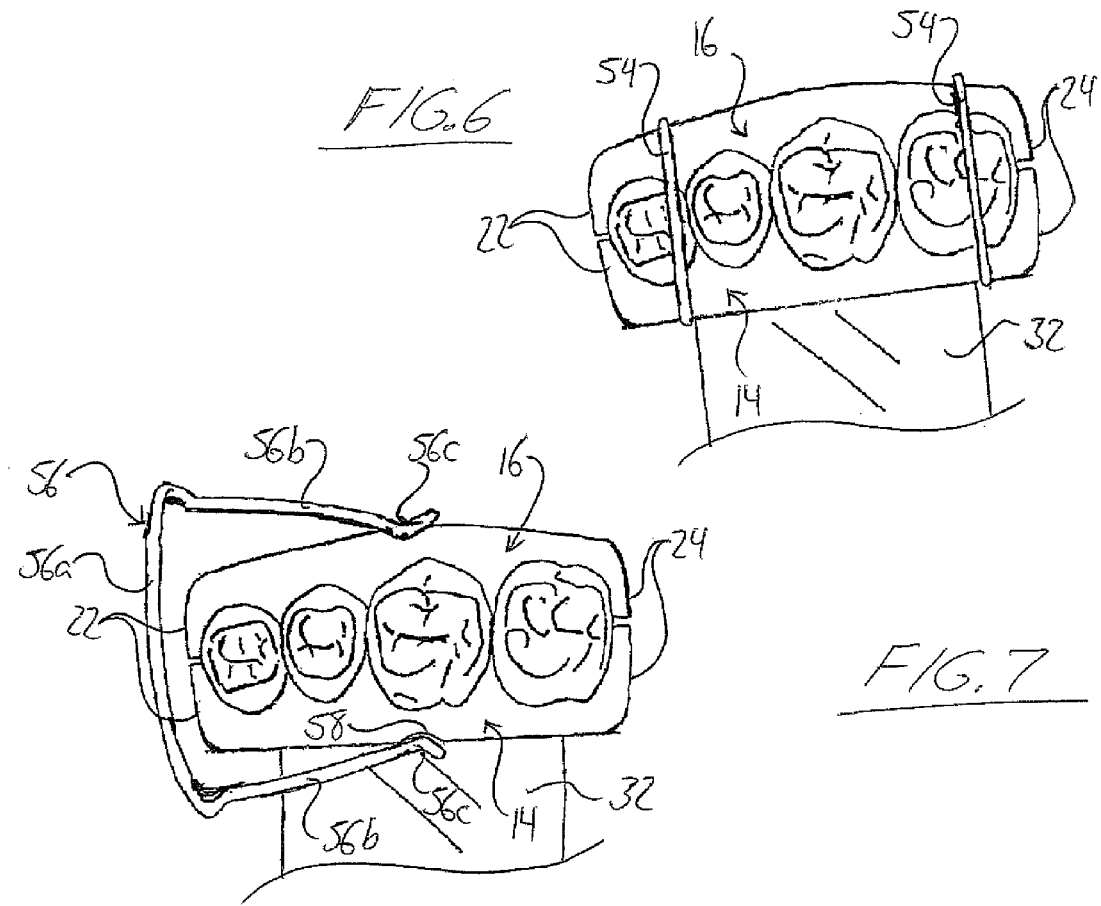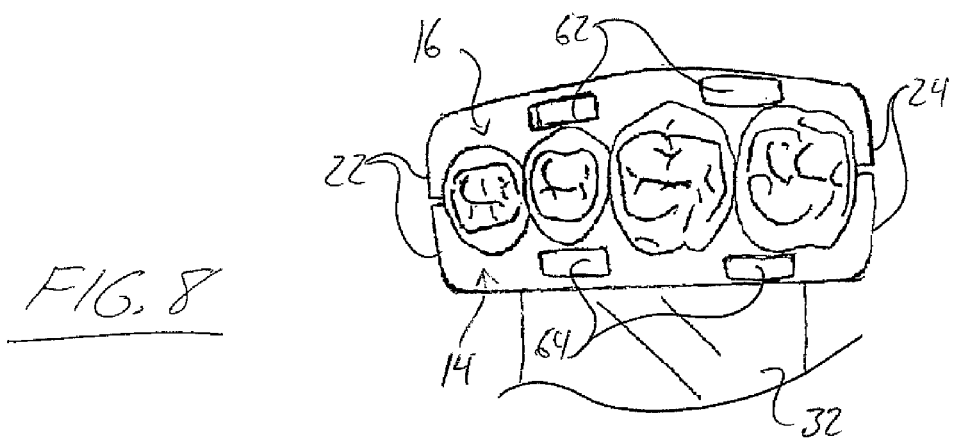

SYSTEMS AND METHODS FOR SETTING PROSTHETIC POSTERIOR TEETH IN DENTURE PRODUCTION

This application claims benefit under 35 U.S.C. 119(e) of U.S. Provisional Patent Application Ser. No. 61/176,966, filed May 11, 2009.

FIELD OF THE INVENTION

The present invention relates generally to the production of dentures, and more particularly to setting of prosthetic posterior teeth in production of dentures.

BACKGROUND OF THE INVENTION

When setting the teeth in a set of upper and lower dentures, the front six (anterior) teeth on both the upper and lower denture can be set uniquely (in no particular set pattern) to achieve the individual look desired for that particular person. However, the posterior teeth (molars and premolars) must be set in accordance to the manufacturer's instructions in order for the teeth to function and perform how they are intended. Typically, proper arrangement of the posterior teeth in this set pattern defined by the manufacturer is difficult and time consuming to achieve. Consequently, setting denture teeth requires someone with the skill and experience to do a good job, but even with such qualified personnel, short cuts and "good enoughs" can and do still happen.

A previous attempt to simplify the denture setting process has resulted in a product known as Filou 28® from Heraeus Kulzer. The product features tooth blocks that receive upper (maxillary) and lower (mandibular) prosthetic posterior teeth from above and below the block into separated upper and lower openings therein. The tooth shaped openings or cavities in the block act to position the individual prosthetic teeth in predetermined positions relative to one another, so that these teeth need not be individually positioned by the technician when setting them in wax on a model produced by mounting of the mandibular and maxillary casts on an articulator to simulate the patient's jaw. It appears that due to the receipt of the maxillary and mandibular teeth in separate cavities from above and below the tooth block, the teeth are not placed in centric occlusion (direct contact) by use of the block, but rather are spaced apart by approximately 2 mm. As a result, achieving centric occlusion requires compensation for this spacing to be made in the articulator pin setting, which appears to rely upon an exclusive articulator assembly. The blocks therefore are not suitable for use with an unmodified conventional articulator, and therefore seem to only form one part of a larger overall system required to implement the labour-reduced denture production process.

It is therefore desirable to provide an alternate way to reduce the time it takes to set the posterior teeth, to eliminate the need for an experienced technician to set the teeth and to improve the precision of the placement of the posterior teeth, while avoiding the need for a specialized articulator.

SUMMARY OF THE INVENTION

According to a first aspect of the invention there is provided a system for setting prosthetic posterior teeth in production of upper and lower dentures, the system comprising:
a pair of tooth blocks, each tooth block comprising:
an inner body having upper and lower rows of inner recesses extending thereinto from one side thereof, the upper and lower rows of inner recesses being respectively contoured to conform to lingual surfaces of maxillary and mandibular prosthetic posterior teeth; and
an outer body having upper and lower rows of outer recesses extending thereinto from one side thereof, the upper and lower rows of outer recesses being respectively contoured to conform to buccal surfaces of the maxillary and mandibular prosthetic posterior teeth;
for each tooth block, the outer body being movable relative to the inner body and securable in a predetermined clamping position in which the upper and lower rows of inner recesses face and respectively align with the upper and lower rows of outer recesses for selectively clamping the maxillary and mandiubular prosthetic posterior teeth between the inner and outer bodies in predetermined positions and orientations relative to one another.

Preferably the inner body of each tooth block has a connection element projecting therefrom to another side thereof opposite the rows of inner recesses and the connection elements are movable relative one another and releasably lockable at different fixed positions relative to one another to facilitate relative positioning of one tooth block relative to the other for positioning of left and right posterior teeth sets relative to one another when carried by opposite ones of the tooth blocks.

Preferably a top surface of one connection element and a bottom surface of another connection element are conformingly shaped with respective to one another for sliding of the connection elements along one another at said top and bottom surfaces.

The top and bottom surfaces may be planar and each connection element may comprise a flat plate. Alternatively, the top and bottom surfaces may be curved and each connection element may comprise a curved plate.

Preferably there is provided a locking device operable to selectively and releasably fix the connecting elements together.

The locking device may comprise a clamping jaw sized to accommodate the connection elements therein for selective clamping together of the connection elements.

There may be provided a remote actuator operable at a distance from the clamping jaw to control a clamping action thereof.

The locking device may comprise a Bowden cable operable to control the clamping jaw.

For each tooth block, the upper rows of inner and outer recesses and the lower rows of inner and outer recesses may be positioned relative to one another to position the maxillary and mandiubular prosthetic posterior teeth in centric occlusion when clamped between the inner and outer bodies.

Preferably there is provided a securing device arranged to secure the outer body of each tooth block to the inner body thereof in the clamping position.

The securing device may comprise resilient bands, each of which is stretchable to fit around the inner and outer bodies of one of the tooth blocks.

Alternatively, the securing device may comprise spring clips, each of which is arranged to clip around an end of the inner and outer bodies of one of the tooth blocks.

In a further alternative, the securing device may comprise magnetically attracted elements carried on opposite ones of the inner and outer bodies of each tooth block to attract one another when the outer body is in the clamping position relative to the inner body.

According to a second aspect of the invention there is provided a method for setting prosthetic posterior teeth in production of upper and lower dentures, the method comprising the following steps:

(a) providing a pair of tooth blocks, each tooth block comprising an inner body having upper and lower rows of inner recesses extending thereinto from one side thereof and an outer body having upper and lower rows of outer recesses extending thereinto from one side thereof, the upper and lower rows of outer recesses being respectively contoured to conform to buccal surfaces of the maxillary and mandibular prosthetic posterior teeth and the upper and lower rows of inner recesses being respectively contoured to conform to lingual surfaces of maxillary and mandibular prosthetic posterior teeth;

(b) for each tooth block, clamping the maxillary and mandiubular prosthetic posterior teeth between the inner and outer bodies with the upper and lower rows of inner recesses facing and respectively aligning with the upper and lower rows of outer recesses to place the maxillary and mandiubular prosthetic posterior teeth in predetermined positions and orientations relative to one another, the prosthetic posterior teeth of the two tooth blocks defining respective ones of left and right prosthetic posterior teeth sets;

(c) heating and applying wax to a lower arch defined by a mandibular cast mounted to a lower jaw of an articulator;

(d) positioning each tooth block into the wax on a respective side of the arch of the mandibular cast;

(e) heating and applying wax to an upper arch defined by a maxillary cast mounted to an upper jaw of an articulator;

(f) closing the articulator;

(g) cooling the wax;

(h) releasing the inner and outer bodies of the tooth blocks from the lingual and buccal surfaces of the prosthetic posterior teeth sets; and (i) opening the articulator.

The method may include, between steps (b) and (d), positioning the left and right prosthetic posterior teeth sets in a desired position relative to one another and fixing said teeth sets in said desired position. This may include relative shifting and subsequent locking together of connection elements projecting from sides of the inner bodies of the tooth blocks opposite the outer bodies thereof, in which case step (h) preferably comprises releasing the locking together of the connection elements by releasing a locking device through an opening left between the maxillary and mandibuler casts at open ends of the upper and lower archs defined thereby.

BRIEF DESCRIPTION OF THE DRAWINGS

In the accompanying drawings, which illustrate exemplary embodiments of the present invention:

FIG. 1 is a schematic overhead plan view of a pair of denture setting tooth blocks according to the present invention in a partially exploded state separated from one another but each assembled to support a respective tooth set.

FIG. 2 is a schematic perspective view of the tooth blocks of FIG. 1 in another partially exploded state interconnected with one another but each having an outer body piece thereof exploded away from an inner body piece thereof and the respective tooth set.

FIG. 3a is a schematic illustration of an impression cast usable with the tooth blocks.

FIG. 3b is a schematic illustration of how the tooth blocks are movable relative to one another to adjust the angle and distance therebetween to fit with a particular patient's jaw configuration, as represented in the figure by an impression cast.

FIG. 5 is a schematic cross-sectional view of the casts and one of the tooth blocks of FIG. 4 during setting of the tooth sets.

FIG. 6 is a schematic partial overhead plan view of a tooth block illustrating use of resilient bands to retain the inner and outer bodies thereof together during use.

FIG. 7 is a schematic partial overhead plan view of a tooth block illustrating use of a spring clip to retain the inner and outer bodies thereof together during use.

FIG. 8 is a schematic partial overhead plan view of a tooth block illustrating use of magnetic members to retain the inner and outer bodies thereof together during use.

DETAILED DESCRIPTION

Figure 4:
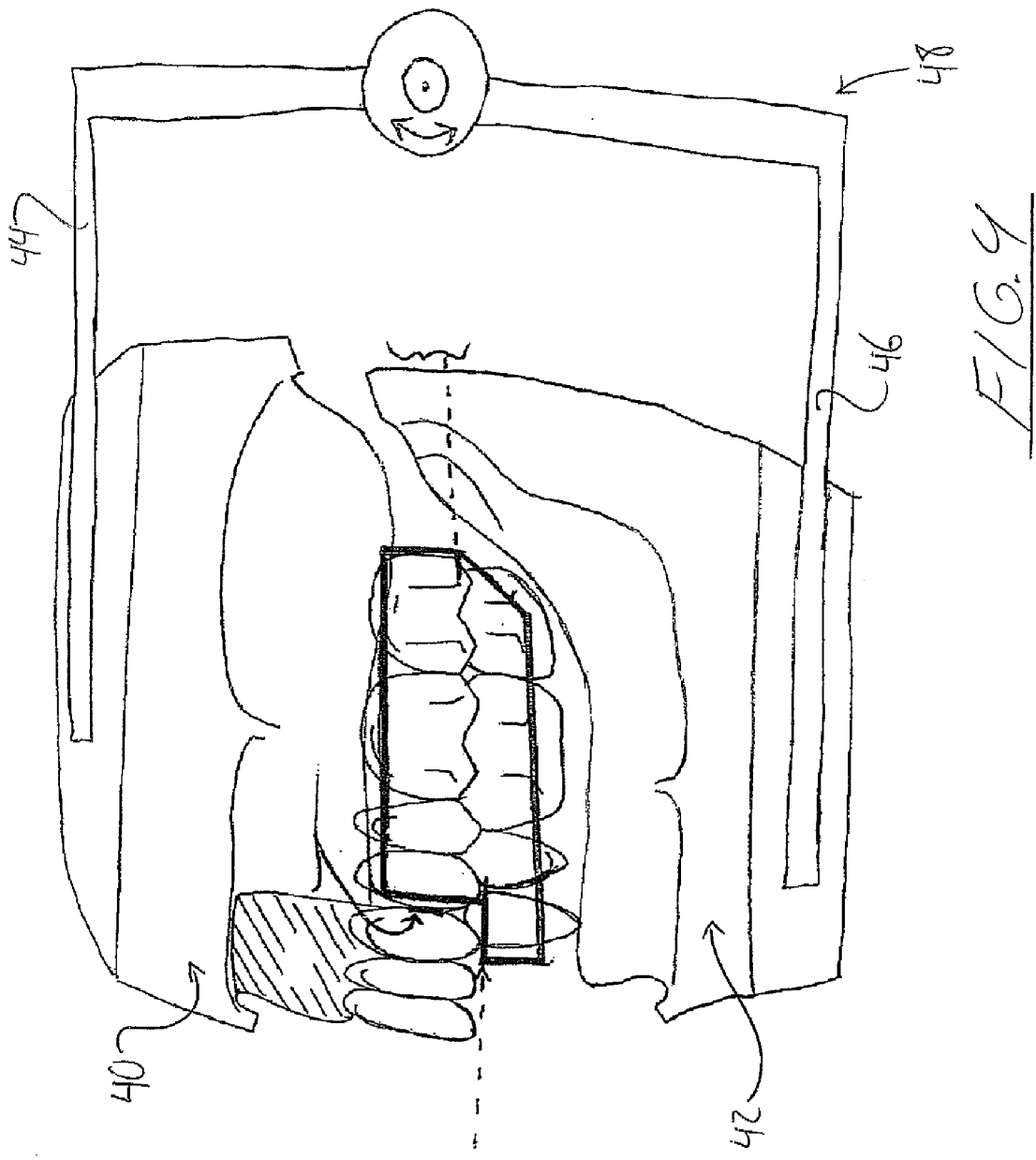
FIG. 4 is a schematic illustration of one of the tooth blocks of FIGS. 1 to 3 in conjunction with maxillary and mandibular casts mounted on an articulator for use in a tooth setting method according to the present invention.

FIG. 1 shows left and right tooth blocks 10a, 10b for use in setting posterior teeth during production of upper and lower dentures for a patient. The left tooth block 10a carries a left side set of prosthetic posterior teeth 12a and the right tooth block 10b carries a right side set of prosthetic poster teeth 12b. Each tooth block 10a, 10b features an inner body piece 14a, 14b and a respective outer body piece 16a, 16b. Each body is a three dimensional piece of solid rigid material having flat top and bottom edges 18, 20 extending in a longitudinal direction establishing a longitudinal dimension of the body in which the body is longer than in its other two dimensions, as represented by longitudinal axis L in FIG. 2. End edges 22, 24 interconnect the top and bottom edges 18, 20 at the opposite ends thereof, and the outward appearance of the body is completed by two opposing sides facing laterally away from the edges. At one these two sides, each body may present a planar face 26.

In a side of each body piece opposite the possibly planar face 26 thereof are upper and lower rows of recesses 28, 30 extending into the body from this side. Each row extends along the longitudinal dimension of the body, the recesses in the row being situated side-by-side therealong between the opposing ends of the body. As perhaps best illustrated by the right side outer body piece 16b of FIG. 2, the recesses of the top row 28 are open at the top edge 18 of the body and the recesses of the bottom row 30 are open at the bottom edge 20 of the body. The boundaries of each recess are shaped and contoured to conform to a corresponding surface of a corresponding tooth among a corresponding row of a corresponding one of the left and right side prosthetic posterior teeth sets. The recesses of the upper row of each outer body conform to the lateral (buccal) surfaces of the upper (maxillary) teeth of the respective one of the left and right side teeth sets, while the recess of the lower row of the same outer body conforms to the lateral (buccal) surfaces of the lower (mandibular) teeth of the same teeth set. In the corresponding inner body, the recesses of the upper row conform to the medial (lingual) surfaces of the upper (maxillary) teeth of the same teeth set, and the recesses of the lower row conform to the medial (lingual) surfaces of the lower (mandibular) teeth of the same set.

To prepare each tooth block 10a, 10b for use, the teeth of the respective set of prosthetic posterior teeth are individually placed into the corresponding recesses of the tooth block's inner body 12a, 12b to seat the medial (lingual) surfaces of these teeth against the correspondingly contoured surfaces of the recesses, which have been carefully positioned and oriented relative to one another so that such placement of the teeth into form fitting seated positions in the recesses places the prosthetic posterior teeth into the relative spatial relationships prescribed by the manufacturer of the teeth. The outer body, which is of equal length and height to the inner body, is then positioned to align the ends of the two bodies and the top and bottom edges of the two bodies so that the recesses of the two bodies align in their respective pairs, facing one another from opposite sides of the teeth seated in the inner body recesses. So aligned with the inner body piece, the outer body piece is moved toward the inner body piece to seat its recesses against the corresponding teeth at the lateral (buccal) surfaces thereof. The two bodies of the block are then locked together to hold them in these form-fitting positions engaged against opposite sides of the respective set of teeth so that the teeth are clamped between the bodies and thereby retained in their prescribed spatial relationships with one another.

As demonstrated by FIG. 2, when the teeth are properly seated an clamped between the bodies of the tooth block, each tooth of the upper (maxillary) row projects upwardly from its biting (occlusal) surface past the top edges 18 of the bodies and each tooth of the lower (mandibular) row projects downwardly from its biting (occlusal) surface past the bottom edges 20 of the bodies, the top and bottom edges extending linearly in the shared longitudinal direction of the aligned bodies clamping the teeth between them. The teeth are also positioned with teeth of the upper (maxillary) row in direct contact (centric occlusion) with the teeth of the lower (mandibular) row.

Projecting from each of the inner bodies 14a, 14b of the two tooth blocks 10a, 10b from the optionally flat-faced side of the body opposite the rows of teeth recesses is a flat connecting plate 32a, 32b having its width oriented parallel to the longitudinal direction of the inner body and its length perpendicular thereto. Planar top and bottom surfaces on each connecting plate 32a, 32b allow sliding of one plate over another, particularly sliding of the connector plate 32b of the right side tooth block 10b over the connector plate 32a of the left side tooth block 10a in the illustrated embodiment, although the opposite configuration would also function in the same manner. The height along one tooth block inner body at which the respective one of the connector plates projects therefrom is offset from the height along the other tooth block inner body at which the other connector plate projects therefrom by the thickness of this other plate, so that when the one plate is disposed flat atop the other, a single horizontal occlusal plane passes through the meeting the of the upper (maxillary) and lower (mandibular) teeth at both the left and right side tooth blocks.

With reference to FIG. 3b, the widths of the connecting plates 32a, 32b span a substantial portion of the length of the tooth blocks and the plates can be slid over one another to adjust both a distance between the tooth blocks in the horizontal plane at which the plates slid over one another and a relative angle between the tooth blocks in this plane. This way the relative angle and spacing between the left and right teeth sets can be adjusted to best fit a particular patient's arch shape, as schematically represented by in FIG. 3a by an impression casting 34 in FIG. 3a.

Referring back to FIG. 1, the connecting plates 32a, 32b may feature a cooperative projection and slot pairing in which a peg 36 projects perpendicularly upward from the lower connection plate 32a and an elongate slot 38 of width slightly exceeding the diameter of the peg's shaft or stem is formed in the upper connection plate 32b. As illustrated by the broken line position of the left side tooth block 10a and respective connection plate 32a in FIG. 1, the peg 36 on this connection plate 32a is passed upward through the slot 38 on the right side connection plate 32b to bring the flat top surface of the left side connection plate 32a into a face-to-face position against the flat bottom surface of the right side connection plate 32b. To adjust the distance between the left and right side tooth blocks 10a, 10b, the peg fixed to the rigid left side connecton plate 32a, which in turn is fixed to the rigid inner body 14a of the left side tooth block 10a, can be slid along the slot 38 in the rigid right side connection plate fixed to the inner body 14b of the right side tooth block 10b to linearly displace the left side tooth set 16a relative to the right side tooth set 16b in a direction perpendicular to the longitudinal directions of the tooth blocks to move the tooth blocks together or apart. To adjust the angle between the tooth blocks 10a, 10b, the connection plates 32a, 32b can be pivoted relative to one another about the axis of the peg projecting through the slot 38. When the desired spatial relationship between the left and right side teeth sets is achieved, the connecting plates 32a, 32b can be clamped together from opposing top and bottom sides thereof to lock this relative positioning of the teeth sets.

Having achieved and locked the desired positioning of the tooth blocks for a particular patient based on modeling of their jaw using maxillary and mandibular impression casts 40, 42 mounted to the upper and lower jaw pieces 44, 46 of an articulator 48, heated wax is applied the mandibular impression cast 42 fixed to the lower jaw piece 44 of the open articulator and the closed teeth blocks fixed together through the connecting plates are lowered into place to set the lower (mandibular) rows of the left and right side teeth sets into the wax in the desired position on the mandibular impression cast 42. During or after cooling of the wax on the mandibular impression cast, heated wax is applied to the maxillary cast carried on the upper jaw piece of the open articulator, which is then closed to bring this wax down into contact with the upper (maxillary) rows of the left and right side teeth sets, taking care not to move the teeth. The tooth blocks and articulator are then left in place to allow the wax to cool and harden.

This process of setting the posterior prosthetic teeth is part of a larger overall method of producing upper and lower dentures by setting all of the prosthetic teeth to be included therein, including the anterior teeth set in a conventional manner on an individual basis, unlike the posterior teeth set with the tooth blocks of the present invention. As in conventional denture setting, the posterior teeth should be on the same plane as and in line with (not too wide or narrow across the medial plane) the upper canines. Therefore it is advisable to set the upper anterior teeth and the block-supported posterior teeth sets in the heated wax at the same time. This way it can be ensured that the posteriors are generally in line with the upper anterior teeth and that the posterior teeth are also set directly over the ridge of the lower (mandibular) cast. Preferably, the upper anterior teeth are positioned first for proper esthetics and the posterior teeth are positioned to align the first posterior tooth to the canine and align the last posterior tooth to an anatomical landmark called the retromolar pad. Once the upper anterior teeth and all the posterior teeth are positioned, the lower anteriors are then added, and the wax is allowed to cool and harden. The anterior and posterior teeth may alternatively be set separately in time. So long as adequate care is taken to ensure everything lines up properly, the results should be expected to be substantially the same.

When the wax has cooled and accordingly dried and hardened to retain the portions of the teeth projecting upward and downward from the tooth blocks, the inner and outer bodies of the tooth blocks are removed. FIG. 5 schematically shows one of the tooth blocks at this stage. The outer body piece 16 previously held together with the inner body piece 14 to clamp the tooth set 12 in place is released and pulled laterally outward away from the tooth set 12, which now has its rows secured in the dried wax 50, 52 on the impression casts. Similarly, the inner body piece 14 is drawn medially inward away from the tooth set 12 to move further inside the cavity defined between the closed-together impression casts by releasing the clamped together connecting plates 14 from one another and sliding them over one another to pull the inner body pieces of the two tooth blocks together toward the medial plane of the jaw model. As shown in FIG. 5, the contours of the teeth may be such that attempts to open the articulator prior to this removal or loosening of the inner and outer tooth blocks from against the medial (lingual) and lateral (buccal) surfaces of the teeth will be resisted by the contoured surfaces of these bodies that conform to the teeth. Attempts to force opening of the articulator without such removal or loosening of the tooth block bodies may dislodge the teeth from their properly set positions within the dried wax.

As shown in FIG. 5, the top and bottom edge 18, 20 of each body piece of each tooth block may slope obliquely upwardly and downwardly, respectively, from the horizontal plane of the connecting plates 32 to diverge away from one another moving away from the teeth 12. This tapering of the height of each tooth block body from the side thereof opposite the teeth recesses to the side of the tooth block body with the teeth-conforming recesses reduces resistance to the withdrawal of the body from the wax on the impression casts. Once all the tooth block bodies have been removed from tight fitting engagement against the teeth now set in the wax, the articulator can be opened. Even with the anterior tooth setting of the denture production process being carried out in a conventional manner, the overall process benefits from reduced time and difficulty compared to conventional methods of individually positioning each and every tooth, without requiring use of a specialized articulator or modification of a conventional articulator. Different models of the tooth blocks can be produced for different brands of teeth, and tooth blocks can be distributed or sold with orders of teeth or sold separately therefrom.

FIGS. 6 to 8 illustrate different arrangements by which the inner and outer bodies 14, 16 of each tooth block can be releasably secured together in a clamping configuration sandwiching the prosthetic posterior teeth 12 between them.

In the embodiment of FIG. 6, each tooth block uses a pair of resilient bands 54, for example orthodontic elastics, sized to be stretchable to fit around the tooth block bodies 14, 16 and tooth set 12 clamped therebetween when the block bodies are brought together after seating of the teeth in the inner body's recesses. The resiliency of the elastic bands biases the outer body 16 toward the inner body 14, thereby clamping the teeth 12 between the bodies in the proper relative positions established by the form fitting contours of the tooth recesses in the tooth block bodies. Each of the two bands encloses about the block bodies and teeth at a position between a respective one of the ends 22, 24 of the tooth block and a respective side of the connecting plate 32 closest thereto. When the setting of the posterior teeth in the wax is completed and the user wishes to open the articulator, the resilient bands can simply be cut from outside the impression casts to release the tooth block bodies from one another for removal of the outer body and loosening of the inner body from against the medial (lingual) surfaces of the respective tooth set 12.

In the embodiment of FIG. 7, each tooth block uses a spring clip 56 that is vertically situated between the top and bottom edges of the tooth block bodies 14, 16. A central portion 56a of the spring clip 56 spans horizontally across the combined width or thickness of the fitted-together tooth block bodies 14, 16 and teeth 12 at the anterior end 22 of the block and a pair of spring legs 56b project horizontally from opposite ends of the central portion 56a on opposite sides of the tooth block toward the opposite tooth block posterior end 24. The legs 56b are resiliently biased toward one another, and thus each engage against a respective tooth block body 14, 16 at the face or side thereof opposite the teeth 12 positioned between the two bodies, thereby clamping the teeth between the bodies being forced together by the spring legs. As shown, a shallow concave dip or groove 58 curving a short distance along the lengthwise dimension of each tooth block body at the lengthwise center thereof may be formed in the spring-engaged side thereof to receive a curved or bent portion 56c of each spring leg 56b defining the clamping portion of the spring leg. The engagement of the curved or bent spring portion with the dip 58 resists sliding of the spring toward and off the anterior end 22 of the tooth block. When the setting of the posterior teeth in the wax is completed and the user wishes to open the articulator, the spring clip can be pulled off the anterior end of the tooth block through the space left between the maxillary and mandibular casts on the articulator jaws.

In the embodiment of FIG. 8, each tooth block features magnetically attracted members 62, 64 disposed in the two tooth block bodies 14, 16 so that the two bodies are attracted together as the outer body 16 is brought toward the inner body 14 and into the clamping position. The magnetically attracted members may include magnets in one body and pieces of ferromagnetic material in the other, or may have magnets in both bodies with their poles oriented so that the magnets of the opposing pieces attract one another when the bodies are brought together with the teeth-conforming recesses of the two bodies facing together. When the setting of the posterior teeth in the wax is completed and the user wishes to open the articulator, the outer body piece 16 can be pulled away from the teeth 12 from outside the impression casts with sufficient force to overcome the magnetic attraction. The magnetically attracted members or elements may be received in cavities extending into the bodies from peripheral surfaces thereof or may alternatively be embedded within the bodies during production thereof.

The blocks that have already been fabricated were done so by producing a posterior tooth set up according to the manufacturer's prescribed set up specifications, but using a material which does not need to be heated up in order to be manipulated, unlike the wax typically used in denture production. This eliminated dimensional change issues that arise from the heating and cooling of such wax. Once the set up was completed according to the manufacturers directions, the teeth were incased (in occlusion) with a viscous material which was later hardened with ultra violet light. This produced a tooth block having the respective set of teeth inside. The block was cut open into 2 pieces, each representing approximately half of the so-formed block, the teeth were removed, and the block pieces were then trimmed to desirable contours and dimensions. It will be appreciated that other materials and production methods may be utilized, for example to produce teeth blocks cast out of metal. It may also be possible to perform the set up on a computer, for example by using a 3d scanner to scan each tooth and then arranging the teeth in the appropriate set up on the computer.

The embodiments of FIGS. 1 to 8 have been described as having flat or planar connection plates 32, which are suitable for setting of prosthetic posterior teeth intended to be set on the basis of a horizontal occlusal plane common to both the left and right sides. However, those of skill in the art will appreciate that not all prosthetic posterior teeth are intended for setting it this manner.

Figure 9:
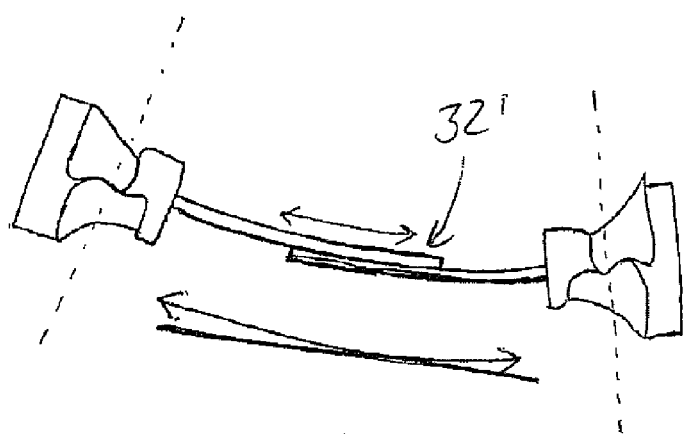
FIG. 9 is a schematic cross-sectional view of an alternate embodiment pair of tooth blocks illustrating adjustment of the relative positions therebetween.
Figure 10:
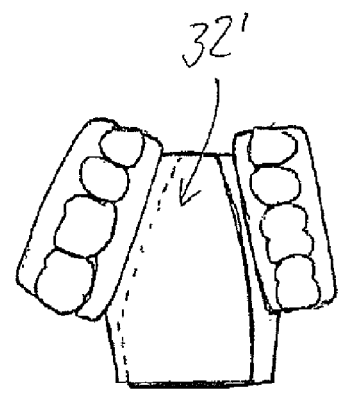
FIG. 10 is a schematic overhead plan view of the tooth blocks of FIG. 9.

FIGS. 9 and 10 schematically illustrate an alternate embodiment where the connection plates 32' are not planar, and instead have curvature to them. The connection plates 32' are again of equal and uniform thickness and again have their connections to the inner bodies of the two teeth blocks offset from one another by the plate thickness to maintain the two teeth blocks at equal positions across the sliding interface between the two connecting plates. However, the connection plates 32' of this embodiment have curved top and bottom surfaces, the top surface of the lower one of two plates having a curvature generally equal to the bottom surface of the upper plate to allow sliding of the top plate over the bottom plate. The connection plates of FIG. 10 span the full length of the tooth blocks and continue onward past the posterior ends thereof, but not past the anterior ends thereof. This embodiment is intended for use with prosthetic tooth sets for which the template to be used as a guide in setting of the teeth according to the manufacturer's prescribed specifications is a curved, rather than flat, plate.

Each of the systems described above aligns, aims and positions the upper and lower posterior teeth in perfect centric occlusion for an upper and lower denture. The systems each feature two "tooth blocks" which separate into halves (used herein to denote pieces that combine, and not being limited to pieces each constituting exactly one half or 50% of the final assembly's weight, volume or other physical characteristic) and rigid connectors which are used in holding the two tooth blocks together during use. The sandwiching the posterior teeth together from the buccal and lingual sides thereof allows all the teeth to be set at once and in proper centric occlusion. The connecting piece which holds the two tooth blocks together can vary in shape according to the tooth manufacturers instructions for tooth set up. For example, most TRUBYTE teeth will require a connector which stays exactly fiat and parallel with is opposite half at all times, as provided by the connecting elements of the embodiments of FIGS. 1 to 8. However, for IVOCLAR teeth, the connector must not be flat and parallel but it must have a certain degree of curvature to it, like the embodiment of FIGS. 9 and 10.

In use, the tooth blocks are opened and the appropriate teeth are inserted into the predetermined patterns set out by the tooth-shaped recesses in the block pieces according to the tooth manufacturer's denture setting specifications. The tooth blocks are closed, and then manipulated (slid open/apart, slid closed/together, and/or swiveled side to side) through the connection elements to obtain the desired settings. The connector is then locked to maintain those settings. Warm wax is applied to the lower arch and the blocks are placed in proper position overtop of the wax. Additional warm wax is applied to the upper arch and articulator is closed, making sure tooth blocks remain in their proper place. The wax is cooled, and the tooth blocks are opened. The connection elements between the tooth blocks are contracted together to pull the inner block pieces from the teeth now set in the wax and the articulator is opened to remove the system from the articulator.

Figure 11:
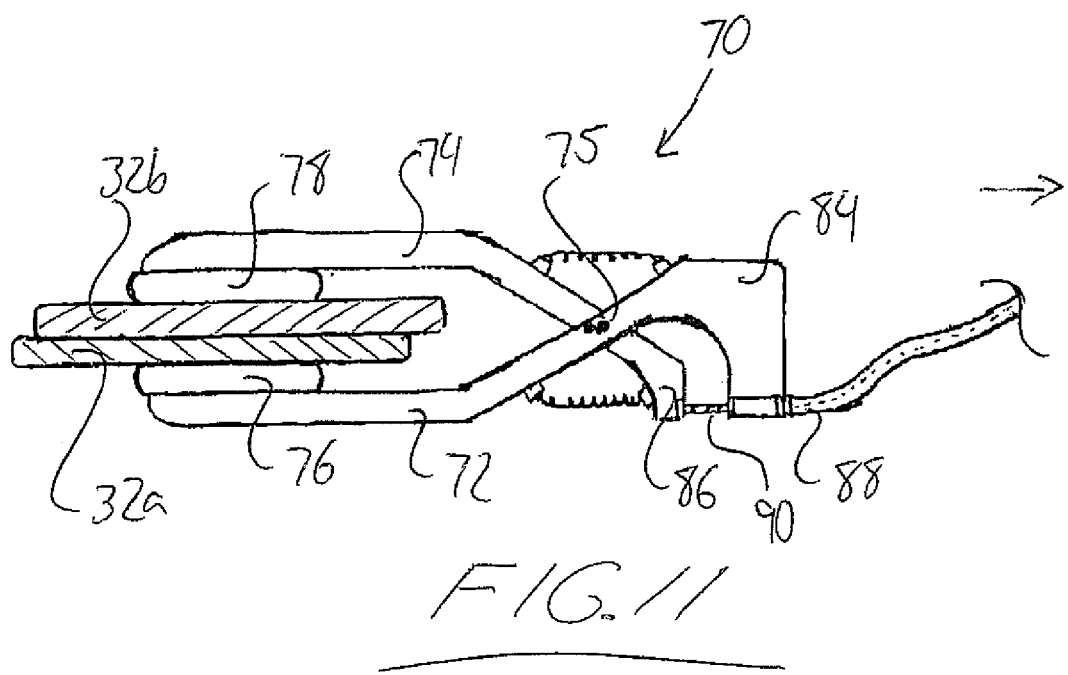
FIG. 11 is a schematic illustration of a locking mechanism clamping together connection plates of the tooth blocks of FIGS. 1 to 5 after adjustment of the relative positions thereof to maintain such positions during setting of the tooth sets on the articulater.

FIG. 11 shows an example of a clamping mechanism 70 that may be used to lock the connecting plates 32a, 32b together once the desired relative positioning of the left and right tooth sets has been achieved, so that this positioning is then retained during setting of tooth sets in wax on the impression cast models on the articulator. The mechanism is similar in structure to a bicycle side-pull single-pivot caliper brake. A pair of arms 72, 74 cross at a single pivot point 75 where they are pivotally fastened together. First ends of the arms 72, 74 carry resilient pads 76, 78, while opposite second ends of the arms feature extensions 84, 86 that project from their respective arms to a common side of the pivot point 76. The extension 84 of the first arm 72 is situated further to a side of the pivot point 75 opposite the resilient pads 76, 78 than the extension 86 of the second arm 74. A Bowden cable has its outer flexible housing 88 fixed at an end thereof to the extension 84 of the first arm 72, while the inner cable 90 of the Bowden cable is fixed at an end thereof to the extension 86 of the second arm 74. Pulling of the inner cable 90 from its control end (not shown) opposite the arms acts to pivot the pad-carrying ends of the arms together to frictionally engage against the top surface of the top connecting plate 32b and the bottom surface of the bottom connecting plate 32a, thereby clamping the connecting plates together within a clamping jaw formed by the arms.

The clamping mechanism includes two springs 92, each connected between crossing portions of the two arms 72, 74 on a single respective side of the pivot point 75. In the illustrated embodiment the two springs are both extension springs both positioned outside the clamping jaw so that each spring's resistance to pulling apart of its ends biases the clamping jaw of the mechanism to an open position. The pulling of the inner cable 90 of the Bowden cable acts against the spring bias to close the clamping jaw to grip the connecting plates of the tooth blocks between the pads 76, 78. It will be appreciated that compression springs may instead be used at other particular positions on the arms to provide a similar biasing action tending to the close the clamping jaw. A control device at the control end of the Bowden cable may be any control device operable to pull the inner cable relative to the cable housing from the control end thereof and releasably lock the inner cable in this pulled condition to maintain the clamping effect of the arms on the connecting plates of the tooth blocks to lock the tooth blocks in fixed positions relative to one another. The control device may be self-locking, for example a ratcheting lever that automatically locks under pulling of the lever around its pivot in a direction pulling the inner cable, or may require additional user input to lock after manual actuation of the control device, for example a lever pivotally carried on a base and having a movable catch secured to one of the lever or the base for movement by the user into a locking position engaging the other of the lever or base when the lever is pivoted to pull the inner rod and close the clamping mechanism. When the locking of the control device is released, the spring bias opens the clamp and returns the inner cable and operating device to their default non-locking conditions.

It will be appreciated that the clamping mechanism may alternatively be constructed to bias the clamping jaws closed under the action of a resilient biasing member and to open the clamping jaws under a pulling or pushing motion of the control cable.

With connecting plates so clamped to hold the tooth blocks in their desired positions relative to one another, the tooth blocks are placed in the heated wax on the mandibular impression cast so that the clamping mechanism 70 projects from between the tooth blocks past the open end of the mandibular cast's arch. This way, when the articulator is closed to lower the maxillary cast and set the upper teeth into the heated wax carried thereon, the clamping mechanism is accommodated by the open end of the cavity defined between the casts at the posterior ends of the archs thereof. Once setting of the upper and lower teeth in the wax is completed and it is desirable to remove or loosen the tooth block bodies and open the articulator, the pulling force on the Bowden cable's inner cable is released from the control end of the cable, which is remote from the articulator and the clamping jaw inside the cavity formed by impression casts. This removes the clamping force from the connecting plates 32a, 32b and thereby loosens the tight engagement of the tooth blocks' inner body pieces from against the medial (lingual) surfaces of the teeth to allow opening of the articulator.

It will be appreciated that other ways of selectively locking or clamping the connection plates of the tooth blocks together to retain desirable relative positioning thereof may be applied. Also, although the illustrated clamping mechanism is described for use in clamping together the flat planar connecting plates of the embodiment of FIGS. 1 to 8, it will be appreciated that a similar arrangement could be used for the curved plate embodiment of FIGS. 9 and 10. While the gripping pads 76, 78 of FIG. 11 have relatively flat faced surfaces, a modified clamping mechanism for curved plate embodiments would preferably have gripping surfaces of a curvature corresponding to that of the connecting plates.

Figures 12, 13:
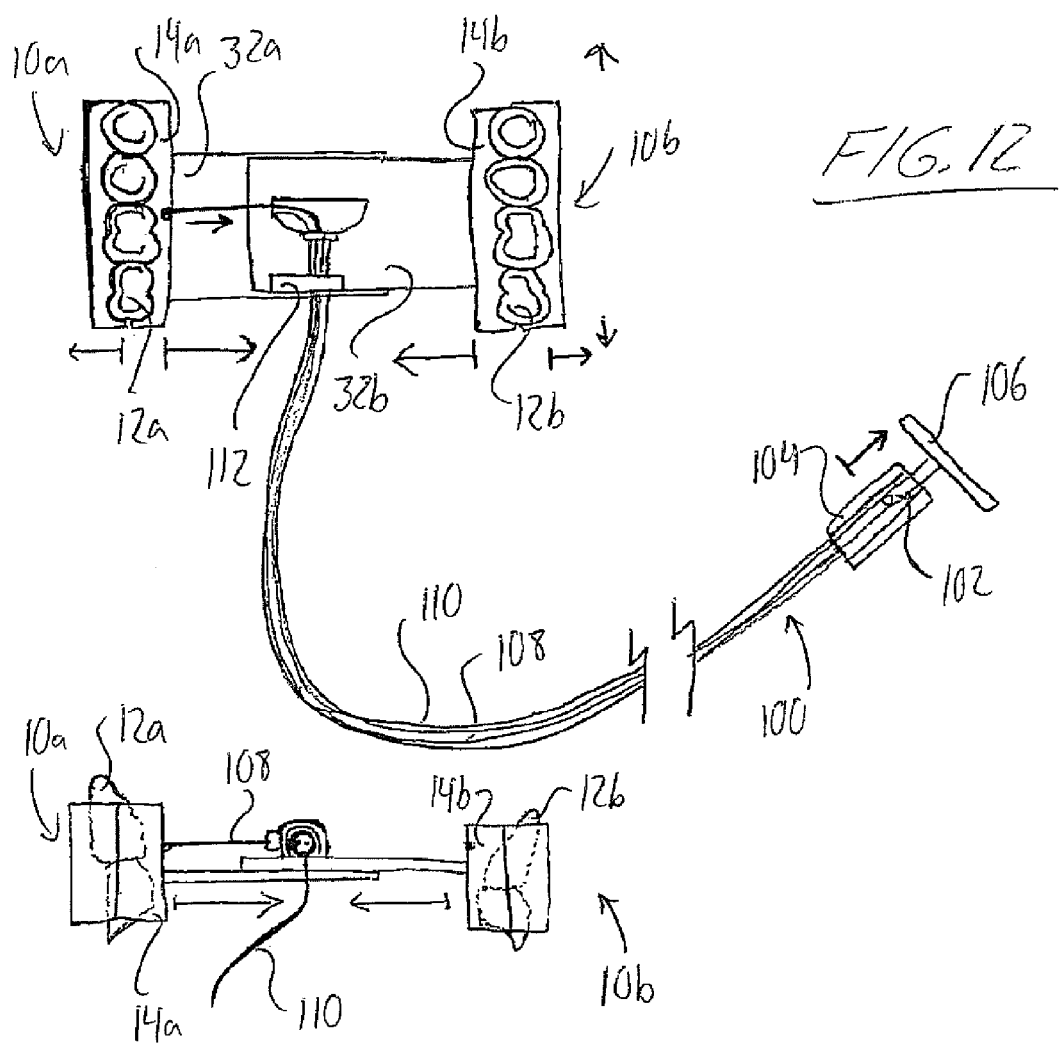
FIG. 12 is a schematic overhead plan view of a release mechanism operable to loosen inner body pieces of tooth blocks of the present invention from against their respective tooth sets after drying of wax into which the teeth are set.
FIG. 13 is a schematic end elevational view of the release mechanism of FIG. 12.

FIGS. 12 and 13 show a release mechanism 100 operable to perform the loosening of the engagement of the inner body pieces 14a, 14b from against the medial (lingual) surfaces of the posterior teeth once the wax has hardened to facilitate safe opening of the articulator without detriment to the set posterior tooth positions. The release mechanism includes a piston rod 102 having one end slidably disposed within the bore of a hollow cylinder 104 and having a cross-member projecting diametrically outward from the piston rod at its opposite end to define a handle 106. The end of piston rod 102 inside the cylinder 104 has a flexible cable 108 fixed thereto. A flexible tubular cable sheathing or housing 110 has one end thereof fitted to the cylinder 104 around the open end thereof opposite that from which the piston rod 104 projects to carry the handle 106. At or proximate its other end, the cable housing 110 is fixed to a mounting element 112 that is turn fixed to the top surface of the top connecting plate 32b of one of the tooth blocks 10b. Toward the end of the cable 108 opposite the piston rod 104, the cable 108 projects from the plate-mounted end of the housing 110, where it turns to extend to the inner body 14a of the tooth block 10a opposite that which has its connecting plate 32b coupled to the cable housing 110 at an approximately central position across the width of the top connecting plate 32b. The end of the cable 108 opposite the piston rod 104 is fixed to the side of the inner body 14a opposite the teeth recesses at a generally central position along the lengthwise dimension of the tooth body 10a.

When the wax has hardened to the teeth in the two teeth blocks and it is desirable to open the articulator, first the clamping jaw or other device used to the lock the connecting plates 32a, 32b together during setting of the teeth is released. However, the dried wax may hold the inner body pieces 14a, 14b of the tooth blocks 10a, 10b in their current positions tight against the medial (lingual) surfaces of the posterior teeth. To loosen these inner body pieces from this condition, the handle 106 of the release mechanism 100 is pulled away from the cylinder 104. Under this action, the cable 108 extending into the cavity between the casts of the jaw model through the open rear end of this cavity pulls on the inner body 14a of the tooth block 10a in a direction toward the inner body 14b of the opposite tooth block 10b due to the fixed coupling of the cable housing end and cable end to opposite ones of these inner bodies 14a, 14b. Sliding between the connecting plates 32a, 32b thus occurs, relatively moving the bottom connecting plate 32a further under the top connecting plate 32b, thereby contracting the overall length of these plates across the medial plane of the cavity and correspondingly reducing the distance between the inner tooth block bodies 14a, 14b. While this pulling may not alone loosen both inner bodes away from their respective tooth sets, the contraction of the overall length of the overlapping connecting plates 32a, 32b acts to reduce the overall width of the tooth setting system components inside the cavity. This gives room to gently move or wiggle the unfreed inner body to loosen it from its engagement against the respective tooth set if necessary.

As an alternative to a releasing or loosening mechanism operable to contract the connecting plates to relatively move the inner bodies closer to one another after drying of the wax, the unlocking of the connecting plates from one another, for example by opening the clamping jaw of the illustrating locking mechanism and withdrawing the clamping jaw from the cavity through the open rear end thereof, may be sufficient to allow gentle wiggling or pulling free of the inner bodies from their respective sides of the jaw model toward the medial plane thereof through the open rear end of the cavity, if necessary. Small tools or utensils, such as needle nose pliers, may be helpful in this process. It will also be appreciated that a dedicated step of loosening one or each inner body from its respective tooth sets may not always be required.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A system for setting prosthetic posterior teeth in production of upper and lower dentures, the system comprising:
a pair of tooth blocks, each tooth block comprising:
an inner body having upper and lower rows of inner recesses extending thereinto from one side thereof, the upper and lower rows of inner recesses being respectively contoured to conform to lingual surfaces of maxillary and mandibular prosthetic posterior teeth;
an outer body movable relative to the inner body and having upper and lower rows of outer recesses extending into the outer body from one side thereof, the upper and lower rows of outer recesses being respectively contoured to conform to buccal surfaces of the maxillary and mandibular prosthetic posterior teeth; and
a securing mechanism arranged to selectively secure the outer body and inner body together in a clamping condition forcing the one side of the outer body and the one side of the inner body toward one another with the upper and lower rows of inner recesses facing and respectively aligning with the upper and lower rows of outer recesses so that seating of the maxillary and mandiubular prosthetic posterior teeth in the upper and lower rows of recesses in the inner body or outer body and securing of the inner body and outer body together in the clamping condition will place the maxillary and mandiubular prosthetic posterior teeth in predetermined positions and orientations relative to one another through clamping of the inner and outer recesses of the inner and outer bodies of the tooth block respectively against the lingual and buccal surfaces of the maxillary and mandibular prosthetic posterior teeth.

2. The system according to claim 1 wherein the inner body of each tooth block has a connection element projecting therefrom to another side thereof opposite the rows of inner recesses and the connection elements are movable relative one another and releasably lockable at different fixed positions relative to one another to facilitate relative positioning of one tooth block relative to the other for positioning of left and right posterior teeth sets relative to one another when carried by opposite ones of the tooth blocks.

3. The system according to claim 2 wherein a top surface of one connection element and a bottom surface of another connection element are conformingly shaped with respect to one another for sliding of the connection elements along one another at said top and bottom surfaces.

4. The system according to claim 3 wherein the top and bottom surfaces are planar.

5. The system according to claim 3 wherein the top and bottom surfaces are curved.

6. The system according to claim 2 wherein each connection element comprises a flat plate.

7. The system according to claim 2 wherein each connection element comprises a curved plate.

8. The system according to claim 2 further comprising a locking device operable to selectively and releasably fix the connecting elements together.

9. The system according to claim 8 wherein the locking device comprises a clamping jaw sized to accommodate the connection elements therein for selective clamping together of the connection elements.

10. The system according to claim 9 comprising a remote actuator operable at a distance from the clamping jaw to control a clamping action thereof.

11. The system according to claim 9 wherein the locking device comprises a Bowden cable operable to control the clamping jaw.

12. The system according to claim 1 wherein, for each tooth block, the upper rows of inner and outer recesses and the lower rows of inner and outer recesses are positioned relative to one another to position the maxillary and mandiubular prosthetic posterior teeth in centric occlusion when clamped between the inner and outer bodies.

13. The system according to claim 1 wherein the securing mechanisms comprise resilient bands, each of which is stretchable to fit around the inner and outer bodies of one of the tooth blocks.

14. The system according to claim 1 wherein the securing mechanisms comprise spring clips, each of which is arranged to clip around an end of the inner and outer bodies of one of the tooth blocks.

15. The system according to claim 1 wherein the securing mechanisms comprise magnetically attracted elements carried on opposite ones of the inner and outer bodies of each tooth block to attract one another when the one side of the inner body and the one side of the outer body are brought into proximity with one another.

* * * * *